United States Patent [19]

Sakamoto et al.

[11] Patent Number: 5,227,310
[45] Date of Patent: Jul. 13, 1993

[54] DEVICE AND METHOD FOR ASSAY OF LIQUID SAMPLE

[75] Inventors: Hisashi Sakamoto, Yawata; Shigeki Yamada, Joyo; Hiroshi Taniguchi, Kyoto, all of Japan

[73] Assignee: Kyoto Daiichi Kagaku Co., Ltd., Kyoto, Japan

[21] Appl. No.: 443,206

[22] Filed: Nov. 30, 1989

[30] Foreign Application Priority Data

Dec. 1, 1988 [JP] Japan ................. 63-306435

[51] Int. Cl.$^5$ ............................................. G01N 21/01
[52] U.S. Cl. ........................................ 436/169; 422/56; 422/57; 422/58; 435/14; 435/28; 436/170
[58] Field of Search ................. 436/169, 170; 422/56, 422/57, 58; 435/14, 28, 805

[56] References Cited

U.S. PATENT DOCUMENTS

| 3,791,933 | 2/1974 | Moyer et al. | 422/56 |
| 3,992,158 | 11/1974 | Przybylowicz et al. | 435/14 |
| 4,256,693 | 3/1981 | Kondo et al. | 422/57 |
| 4,271,121 | 6/1981 | Diller et al. | 422/58 |
| 4,333,339 | 6/1982 | McNeely et al. | 422/58 |
| 4,477,575 | 10/1984 | Vogel et al. | 422/56 |
| 4,495,291 | 1/1985 | Lawton | 422/58 |
| 4,587,102 | 5/1986 | Nagatomo et al. | 422/56 |
| 4,631,174 | 12/1986 | Kondo et al. | 435/805 |

FOREIGN PATENT DOCUMENTS

| 113896 | 7/1984 | European Pat. Off. . | |
| 0119623 | 9/1984 | European Pat. Off. | 422/56 |
| 097952 | 11/1986 | European Pat. Off. . | |
| 3510992 | 10/1985 | Fed. Rep. of Germany . | |

Primary Examiner—Robert J. Warden
Assistant Examiner—Timothy M. McMahon
Attorney, Agent, or Firm—Birch, Stewart, Kolasch & Birch

[57] ABSTRACT

A device for colorimetric assay of at least one component in a liquid sample, which device comprises a support having a through hole with an area of from 3 to 80 mm$^2$, a transparent porous film which is provided on the support to cover the hole, a reagent layer provided on a surface of the porous film which is not contacted to the support, and a sample-holding layer which covers the reagent layer and a part of a surface of the support, whereby an amount or concentration of at least one component in the liquid sample may be easily and accurately measured.

8 Claims, 1 Drawing Sheet

DEVICE AND METHOD FOR ASSAY OF LIQUID SAMPLE

BACKGROUND OF THE INVENTION

1. Field of the Invention

The present invention relates to a device and a method for the quick and easy assay of a liquid sample, particularly body liquids, such as whole blood, blood serum, blood plasma, urea and cerebrospinal liquid.

2. Description of the Related Art

For the assay of a particular component in a liquid sample, an enzymatic analysis is widely used since it can be carried out under mild conditions. In clinical tests, the body liquid is analyzed with a reagent solution containing an oxidase which oxidizes a particular component, a pigment precursor and, optionally, a peroxidase. In such an enzymatic analysis, hydrogen peroxide, which is generated through oxidation of the particular component with the oxidase, directly oxidizes the oxidizable pigment precursor or oxidation coupling with the pigment precursor in the presence of the peroxidase to generate a pigment. Then, the generated pigment is colorimetrically measured by, for example, absorptiometry, fluorophotometry and emission spectroscopy, and in turn, the amount or concentration of particular component is indirectly measured.

Examples of the oxidases useful in the clinical tests are glucose oxidase, uricase, cholesterol oxidase, glycerol-triphosphate oxidase, cholin oxidase, acyl-CoA oxidase, sarcosine oxidase, various amino acid oxidases, bilirubin oxidase, lactate oxidase, lactose oxidase, pyruvate oxidase, galactose oxidase, glycerol oxidase and the like.

As the pigment precursor, oxidizable pigment precursors such as a so-called Trinder's reagent (cf. Ann. Clin. Biochem., 6, 24 (1960)), o-anisidine, benzidine, o-tolidine and tetramethylbenzidine are well known.

One of the advantages of the enzymatic analysis resides in that, if the component to be analyzed is changed, the same color developing system can be used by changing the kind of oxidase. Therefore, the application of the enzymatic analysis to various analytical items has been investigated.

Recently, in order to quickly and conveniently carry out the assay, a reagent system fixed on a solid support has been advantageously used in place of the conventional reagent solution.

For example, U.S. Pat. No. 3,630,957 and Japanese Patent Publication No. 33800/1974 disclose a water-resistant test film which comprises a plastic film and a polymer layer in which an assay system comprising the above oxidase and hydrogen peroxide is dispersed. In the assay with such water-resistant test film, since the color of the generated pigment is measured from the side on which the sample, such as the whole blood or the blood serum, is applied, the sample should be wiped out with a piece of absorbent cotton and the like after contacting the sample to the reagent layer for a certain period of time. Further, since the color is developed in the presence of a sufficient amount of oxygen after wiping out of the sample, the test film should be kept standing in the air for a certain period of time.

U.S. Pat. No. 3,992,158 and Japanese Patent Publication No. 21677/1978 disclose a multi-layer test film comprising a liquid-impermeable transparent support, a reagent layer and a spreading layer. When the liquid sample is applied at a point of the spreading layer, it spreads over the spreading layer and then migrates into the reagent layer. The color of the pigment which is generated through the reaction between the specific component and the reagent is measured through the transparent support. Therefore, it is not necessary to remove the applied sample. However, since the reagent layer is present between the support and the spreading layer, it is difficult for the air to reach the reagent layer through the spreading layer. Particularly when the reagent layer contains the oxidase, the reaction does not proceed sufficiently due to shortage of oxygen.

To overcome this drawback, EP-A-137 521 and Japanese Patent Kokai Publication No. 82859/1985 discloses a multi-layer integral element for chemical analysis, which comprises an oxygen-permeable protein-impermeable light shielding layer between the reagent layer and the spreading layer to improve the contact between the reagent layer and the air. However, since the reagent layer never contacts the air on the support side, oxygen is not sufficiently supplied to the reagent layer.

German Patent No. 3 510 992 and Japanese Patent Kokai Publication No. 205364/1985 disclose an assay device having a porous hydrophobic oxygen-supplying layer between the reagent layer and the support. Such a device can significantly increase the amount of oxygen supplied to the reagent layer containing the oxidase. But, since the oxygen-supplying layer has a certain thickness to retain a sufficient amount of oxygen therein, the device has no light-transparency on the support side, so that the color of the generated pigment should be measured from the sample-supplied side of the device.

SUMMARY OF THE INVENTION

One object of the present invention is to provide an assay device which can overcome the above drawbacks of the conventional assay devices.

Another object of the present invention is to provide an assay device which can quickly and easily analyze a particular component in a liquid sample with good accuracy.

A further object of the present invention is to provide a process for analyzing a particular component in a liquid sample using the assay device of the present invention.

According to one aspect of the present invention, there is provided a device for the colorimetric assay of at least one component in a liquid sample, which device comprises a support having a through hole with an area of 3 to 80 mm$^2$, a transparent porous film which is provided on the support to cover the hole, a reagent layer provided on the surface of the porous film which is not contacted to the support, and a sample-holding layer which covers at least a part of the reagent layer and a part of a surface of the support.

According to another aspect of the present invention, there is provided a process for analyzing at least one component in a liquid sample using the assay device of the present invention, which process comprises the steps of applying an amount of the liquid sample on the sample-holding layer so that the sample will penetrate the layer, and colorimetrically measuring a color developed in the reagent layer through the hole of the support from the support side of the device, for example, with a reflectometer.

BRIEF DESCRIPTION OF THE DRAWINGS

The present invention will be illustrated by making reference to the accompanying drawings.

DETAILED DESCRIPTION OF THE PREFERRED EMBODIMENTS

Figure 1:
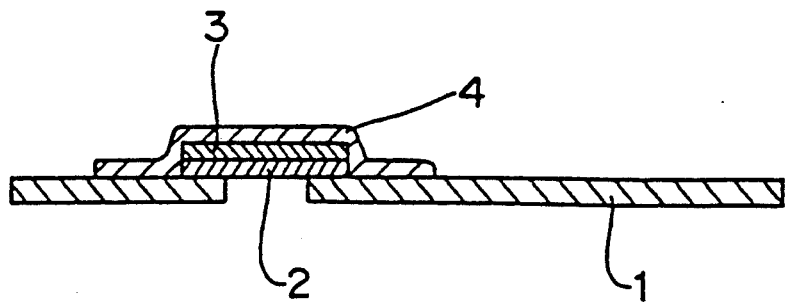
FIG. 1 is a cross section of a first embodiment of the assay device of the present invention.

The assay device of the present invention may be prepared as follows.

A solution or dispersion of the reagent is applied on the transparent porous film and dried to form the reagent layer on the porous film. The composite of the porous film and the reagent layer is placed on the support, facing the porous film to the support to cover the through hole in the support and fixed thereto. Then, the sample-holding layer is provided to cover the reagent layer and fixed to the support. The porous film and the sample-holding layer may be fixed to the support, for example, by thermocompression bonding by using a thermoplastic resin, or with an adhesive double coating tape. Alternatively, only the porous film is fixed to the support and then the reagent layer is formed on the porous film.

The through hole may be of any shape, for example, a round shape, a rectangular shape and the like.

The support may have an additional through hole at a position which is covered only by the sample-holding layer. Through the additional hole, the application of the sample on the sample-holding layer is detected from the support side of the device. This embodiment is advantageous in automatic measurement since a period of time from the sample application to the measurement of the developed color can be kept constant.

Over the sample-holding layer, another support having a through hole may be provided and the sample can be applied through such a hole.

The porous film to be used in the present invention preferably has a porosity of from 2 to 70 %, a pore size of 0.01 to 20 μm and a thickness of 5 to 30 μm. Since the porous film is air permeable, the amount of oxygen necessary for the oxidation reaction can be supplied to the reagent layer from the air. While the porous film has a larger porosity and/or a larger, thickness and has air permeability, it has less transparency. Thus, with the reduced transparency of the porous film, it is difficult or impossible to measure the color developed in the reagent layer through the porous film. Therefore, the transparent porous film to be used in the present invention preferably has a transparency of at least 30%, more preferably at least 60% for the visible light and near UV light, for example, light with a wavelength in the range from about 300 to about 900 nm. The porous film suitable for the present invention is commercially available under the trade name of Newclepore (by Newclepore Ltd.) and Juraguard (by Polyplastic Ltd.). Of course, other suitable transparent oxygen-permeable films can be used in the present invention.

The reagent layer contains the oxidase specific to the particular component to be analyzed, peroxidase and the pigment-precursor. Examples of the peroxidase and the pigment-precursor have already described above.

The reagent layer may further contain light-reflecting water-insoluble particles, which prevent interference with colored components during the analysis of a colored sample such as blood and enables an accurate measurement from the porous film side. Preferably, the light reflecting water-insoluble particles have such a function that they prevent penetration of blood corpuscles into the reagent layer in the analysis of a blood sample. Preferred examples of the light reflecting water-insoluble particles are white pigments such as titanium oxide, zinc oxide, barium sulfate and magnesium oxide. Other particles which reflect light and are insoluble in the liquid sample can also be used. Examples of such particles are fluorocarbons, polystyrene latex particles, calcium carbonate, talc, alumina powder, dextran, acrylic polymer particles and the like.

To improve an application property of the reagent liquid, it may contain a hydrophilic polymer. Specific examples of the hydrophilic polymer are hydroxypropylcellulose, methylcellulose, sodium alginate, polyvinyl alcohol, gelatin, modified gelatin, agar and the like. Penetrability of the reagent liquid is improved by the addition of an emulsion type adhesive or latex particles.

The addition of at least one of nonionic surfactants, plasticizers and stabilizers to the reagent liquid improves the application property and the reactivity of the reagent liquid.

The reagent layer may consist of two sub-layers, one of which contains the enzyme and the color-developing agent and the other of which contains the light reflecting water-insoluble particles.

The sample-holding layer spreads the applied sample over its entire surface and prevents the sample from being spilled due to vibration and the like. The sample-holding layer is preferably made of a fibrous porous material such as filter paper, a fabric, a non-woven fabric and a mesh. The sample-holding layer may contain an anti-coagulating agent, ascorbate oxidase, which prevents interference due to oxidation with possibly present ascorbic acid, or cholesterol esterase which converts an ester type cholesterol to a free cholesterol in the measurement of total cholesterols.

FIG. 1 is a cross section of a first embodiment of the assay device of the present invention which comprises a support 1 having a through hole, a porous film 2 formed on the support to cover the hole, a reagent layer 3 fixed on the porous film and a sample-holding layer 4 fixed on the support to cover the reagent layer 3. The porous film 2 and the sample-holding layer 3 are fixed to the support by a thermoplastic resin or an adhesive double coating tape (not shown).

Figure 2:
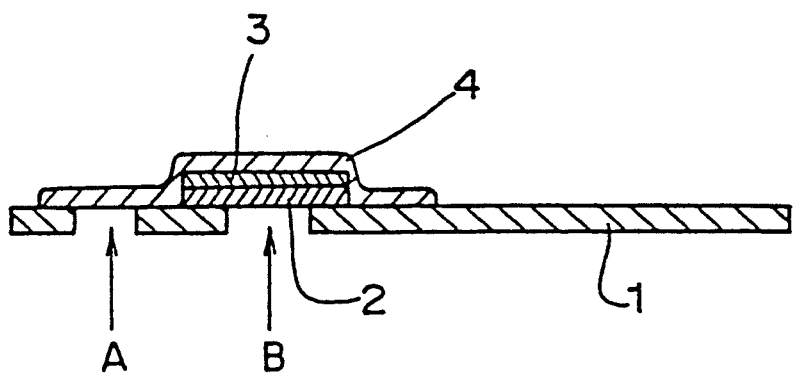
FIG. 2 is a cross section of a second embodiment of the assay device of the present invention.

FIG. 2 is a cross section of a second embodiment of the assay device of the present invention, which is substantially the same as the device of FIG. 1, except that a second another through hole is provided in the support 1 at the position which is covered only with the sample-holding layer 4. For example, in the automatic measurement, the sample application is detected at the position indicated by the arrow A and after a predetermined period of time, the reflectance on the reagent layer 3 is measured at the position indicated by the arrow B.

Figure 3:
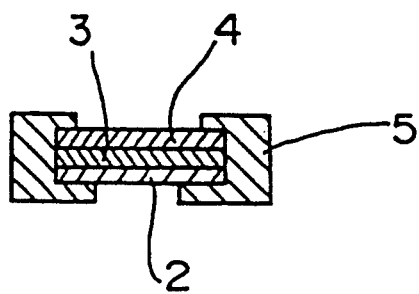
FIG. 3 is a cross section of a third embodiment of the assay device of the present invention.

FIG. 3 is a cross section of a third embodiment of the assay device of the present invention which comprises the porous film 2, the reagent layer 3 formed on the porous film 2 and the sample holding layer 4, all of which are fixed in a mount 5. The mount 5 has one through hole on each of the porous film side and the sample-holding layer side.

In FIGS. 1, 2 and 3, the size in the thickness direction is enlarged for easy understanding.

EXAMPLES

The present invention will be explained in detail by following Examples.

Example 1

Determination of glucose in blood

On a transparent porous film (Newclepore) having a thickness of 10 μm, a reagent liquid having the following composition was applied to a dry thickness of 100 μm and dried at 40° C. for one hour followed by slitting to a width of 7 mm.

| Composition of the reagent liquid | |
|---|---|
| Glucose oxidase | 10 ku |
| Peroxidase | 20 ku |
| 4-Aminoantipyrine | 150 mg |
| N-Ethyl-N-(2-hydroxy-3-sulfopropyl)-3,5-dimethylaniline | 200 mg |
| 0.15M phosphate buffer (ph 7.0) | 2 ml |
| 4% Hydroxypropylcellulose solution | 3 g |
| 50 wt % Solution of titanium oxide | 1 g |

On a support film having a series of through holes each having a diameter of 4 mm and covered with a thermoplastic resin, the porous film sticks were placed with the reagent layer upside covering one of a pair of holes with each stick, and thermocompression bonded. Over each of the other hole of the pair of holes and the respective reagent layers, strips of filter paper each having a width of 10 mm were placed and thermocompression bonded to the support. Then, along the lines between the adjacent two pairs of holes, the laminated film was cut to form assay devices.

For comparison, an assay device was prepared by using a transparent non-porous film in place of the transparent porous film.

On the sample-holding layer of each assay device, 20 μl of whole blood containing glucose in various concentrations was dropped. After one minute, the reflectance at the wavelength of 630 nm on the reagent layer was measured from the porous film side through the hole with an integrating sphere type reflectometer. From the reflectance, the K/S value was calculated according to the simplified Kubelka-Munk equation:

$$K/S = (1-r)^2/2 \times R$$

in which K is a constant, S is a scattering coefficient, and R is reflectance/100. The K/S value is linearly proportional to the molar concentration of glucose in the blood (cf. Gustav-Kortum, "Reflectance Spectroscopy", 106-111, Springer-Verlag, 1969).

The results are shown in Table 1.

TABLE 1

| Glucose concentration (mg/dl) | Present invention | | Comparative | |
|---|---|---|---|---|
| | Reflectance (%) | K/S value | Reflectance (%) | K/S value |
| 0 | 94.5 | 0.002 | 96.3 | 0.001 |
| 75 | 43.6 | 0.365 | 70.8 | 0.060 |
| 158 | 29.7 | 0.832 | 63.5 | 0.105 |
| 290 | 17.6 | 1.929 | 60.3 | 0.131 |
| 386 | 12.8 | 2.970 | 59.8 | 0.135 |

TABLE 1-continued

| Glucose concentration (mg/dl) | Present invention | | Comparative | |
|---|---|---|---|---|
| | Reflectance (%) | K/S value | Reflectance (%) | K/S value |
| 533 | 9.0 | 4.601 | 59.4 | 0.139 |

With the assay device of the present invention, the K/S value increased in proportional to the glucose concentration, while with the comparative assay device, the K/S value did not increase in proportional to the glucose concentration above the concentration of about 150 mg/dl.

Example 2

On a transparent porous film (Juraguard) having a thickness of 25 μm, a reagent liquid having the following composition was applied to a dry thickness of 200 μm and dried at 40° C. for one hour. Then, the assay device was prepared in the same manner as in Example 1.

| Composition of the reagent liquid | |
|---|---|
| Lactate oxidase | 990 u |
| Peroxidase | 23 ku |
| 4-Aminoantipyrine | 50 mg |
| N-Ethyl-N-(2-hydroxy-3-sulfopropyl)-m-toluidine | 200 mg |
| 0.3M phosphate buffer (ph 7.0) | 2 ml |
| 4% Hydroxypropylcellulose solution | 3.7 g |
| 50 wt % Solution of titanium oxide | 1.2 g |
| Nonionic surfactant (10% Triton X-100) | 0.5 ml |

For comparison, an assay device was prepared by using a transparent non-porous film in place of the transparent porous film.

On the sample-holding layer of each assay device, 20 μl of whole blood containing lactic acid in various concentrations was dropped. After one minute, the reflectance at the wavelength of 560 nm on the reagent layer was measured from the porous film side through the hole with an integrating sphere type reflectometer, and the K/S value was calculated as in Example 1.

With the blood plasma obtained from the whole blood by centrifugation, the same measurement was done.

The results are shown in Table 2.

TABLE 2

| Concentration of lactic acid | Present invention | | | | Comparison | |
|---|---|---|---|---|---|---|
| | Whole blood | | Plasma | | Whole blood | |
| | Reflectance | K/S value | Reflectance | K/S value | Reflectance | K/S value |
| 9 | 66.8 | 0.083 | 63.8 | 0.103 | 72.8 | 0.051 |
| 20 | 50.6 | 0.241 | 48.7 | 0.270 | 58.6 | 0.146 |
| 43 | 32.8 | 0.688 | 32.0 | 0.723 | 48.3 | 0.277 |
| 75 | 20.3 | 1.565 | 18.8 | 1.754 | 41.0 | 0.425 |
| 97 | 15.0 | 2.408 | 13.9 | 2.667 | 39.3 | 0.469 |
| 108 | 13.2 | 2.854 | 12.3 | 3.127 | 38.7 | 0.485 |

With the assay device of the present invention, the K/S value increased in proportional to the lactic acid concentration both for the whole blood and the plasma, while with the comparative assay device, the K/S value did not increase in proportional to the lactic acid concentration above the concentration of about 75 mg/dl.

The invention being thus described, it will be obvious that the same may be varied in many wats. Such variations are not to be regarded as a departure from the spirit and scope of the invention, and all such modifications as would be obvious to one skilled in the art are intended to be included within the scope of the following claims.

What is claimed is:

1. A device for colorimetric assay of at least one component in a liquid sample, which device comprises a support having a first through hole with an area from 3 to 80 mm², a transparent porous air-permeable film which is provided on a surface of said support to cover said first through hole, a reagent layer having an inner surface and an outer surface, said inner surface being provided on a surface of said pours film which is not in contact with said support, said reagent layer containing an oxidase capable of oxidizing said at least one component, peroxidase and a pigment-precursor, and a sample-holding layer provided on aid outer surface of said reagent layer, such that said sample-holding layer covers at least a part of said reagent layer and a part of said support.

2. The device according to claim 1, wherein said porous film has a porosity of from 2 to 70%.

3. The device according to claim 1, wherein said porous film has a pore size of from 0.01 to 20 μm.

4. The device according to claim 1, wherein said porous film has a thickness of from 5 to 30 μm.

5. The device according to claim 1, wherein said reagent layer further contains light reflecting water-insoluble particles.

6. The device according to claim 1, wherein said support has a second through hole therein at a position which is covered only by said sample-holding layer.

7. The device according to claim 1, wherein said support comprises two support members having a single through hole which corresponds to each of a porous film side and sample-holding layer side of said device with respect to said reagent layer.

8. A process for analyzing at least one component in a liquid sample using the assay device of claim 1, which process comprises the steps of applying an amount of a liquid sample to said sample-holding layer such that said sample penetrates therein, and colorimetrically measuring a color developed in said reagent layer viewed through said first through hole of said support from the support side of said device.

* * * * *